(12) United States Patent
Hu et al.

(10) Patent No.: US 8,766,002 B2
(45) Date of Patent: Jul. 1, 2014

(54) PREPARATION AND PURIFICATION OF IODIXANOL

(75) Inventors: Zhiqi Hu, Tazhou (CN); Huoying Zhang, Tazhou (CN)

(73) Assignee: Imax Diagnostic Imaging Holding Limited, Wanchai (HK)

( * ) Notice: Subject to any disclaimer, the term of this patent is extended or adjusted under 35 U.S.C. 154(b) by 148 days.

(21) Appl. No.: 13/510,432

(22) PCT Filed: Nov. 26, 2009

(86) PCT No.: PCT/CN2009/001333
§ 371 (c)(1),
(2), (4) Date: Jul. 9, 2012

(87) PCT Pub. No.: WO2011/063551
PCT Pub. Date: Jun. 3, 2011

(65) Prior Publication Data
US 2012/0283474 A1   Nov. 8, 2012

(51) Int. Cl.
C07C 233/05 (2006.01)
C07C 233/65 (2006.01)
C07B 63/00 (2006.01)
C07C 231/24 (2006.01)

(52) U.S. Cl.
CPC ............. *C07C 231/24* (2013.01); *C07B 63/00* (2013.01)
USPC ........................................ 564/153; 424/9.452

(58) Field of Classification Search
USPC ........................................ 564/153; 424/9.452
See application file for complete search history.

(56) References Cited

U.S. PATENT DOCUMENTS

| | | | |
|---|---|---|---|
| 5,204,005 A | 4/1993 | Doran, III et al. | |
| 5,349,085 A | 9/1994 | Hansen et al. | |
| 5,616,795 A | 4/1997 | Mauro et al. | |
| 5,705,692 A | 1/1998 | Wang et al. | |
| 5,763,650 A | 6/1998 | Mauro et al. | |
| 6,187,826 B1 | 2/2001 | Viscardi et al. | |
| 2002/0010368 A1 | 1/2002 | Homestad | |
| 2002/0072639 A1 | 6/2002 | Cervenka | |
| 2008/0214867 A1 | 9/2008 | Cervenka et al. | |
| 2008/0287711 A1 | 11/2008 | Strandmyr | |
| 2008/0300423 A1 | 12/2008 | Homestad | |
| 2009/0253935 A1 | 10/2009 | Cervenka et al. | |
| 2011/0021823 A1* | 1/2011 | Homestad et al. | 564/153 |
| 2012/0083625 A1 | 4/2012 | Homestad | |

FOREIGN PATENT DOCUMENTS

| | | |
|---|---|---|
| CN | 101293855 A | 10/2008 |
| EP | 0108638 A1 | 5/1984 |
| EP | 0470247 A1 | 2/1992 |
| EP | 0902686 B1 | 3/1999 |
| JP | 2000505820 A | 5/2000 |
| JP | 2007521262 A | 8/2007 |
| JP | 2009529491 A | 8/2009 |
| KR | 20050006367 A | 1/2005 |
| KR | 20050024944 A | 3/2005 |
| WO | 9637458 A1 | 11/1996 |
| WO | 9637459 A1 | 11/1996 |
| WO | 9730788 A1 | 8/1997 |
| WO | 9854124 A1 | 12/1998 |
| WO | 9918054 A1 | 4/1999 |
| WO | 0015266 A2 | 3/2000 |
| WO | 0047549 A1 | 8/2000 |
| WO | 2005003080 A1 | 1/2005 |
| WO | 2006016815 A1 | 2/2006 |
| WO | 2007013815 A1 | 2/2007 |
| WO | 2007064220 A1 | 6/2007 |
| WO | 2007073202 A1 | 6/2007 |
| WO | 2007094680 A1 | 8/2007 |

OTHER PUBLICATIONS

Priebe, et al., "Synthesis and Characterization of Iodixanol", Acta Radiologica, 1995, vol. 36, Supplement 399, pp. 21-31.
PCT International Search Report, Application No. PCT/CN2009/001333 dated Sep. 2, 2010.
PCT International Preliminary Report on Patentability, Application No. PCT/CN2009/001333 dated Feb. 24, 2012.
Japanses Office Action, Application No. JP 2012-54029 dated Nov. 26, 2013.

\* cited by examiner

*Primary Examiner* — Shailendra Kumar
(74) *Attorney, Agent, or Firm* — MacMillan, Sobanski & Todd, LLC

(57) ABSTRACT

An improved synthesis method for preparation of iodixanol, and a purification process through macroporous adsorption resin chromatographic column and recrystallization are provided. The synthesis method relates to dimerization of 5-acetamido-N,N'-bis(2,3-dihydroxypropyl)-2,4,6-triiodo-isophthalamide (compound A) to prepare iodixanol, wherein excessive side reactions such as alkylation are effectively inhibited by controlling the pH of the reaction mixture with a boron-containing acidic substance or salts thereof such as boric acid. In this way, the conversion rate of compound A to iodixanol is 85-90%. The iodixanol crude product is purified by a macroporous adsorption resin chromatographic column, obtaining iodixanol product with recovery of 90-95% and purity of 96-98%. The iodixanol crude product is recrystallized in mixed solvent containing 2-methoxyethanol, obtaining iodixanol product with recovery of 90-95% and purity of greater than 99%.

54 Claims, No Drawings

PREPARATION AND PURIFICATION OF IODIXANOL

This application is a 371 of PCT/CN2009/001333, filed Nov. 26, 2009.

TECHNICAL FIELD

This invention belongs to the field of chemical drugs and relates to the methods of preparation and purification of iodixanol (1,3-bis(acetamido)-N,N'-bis[3,5-bis(2,3-dihydroxypropylaminocarbonyl)-2,4,6-triiodo-phenyl]-2-hydroxypropane).

BACKGROUND ART

Iodixanol, trade name Visipaque®, was developed by Nycomed as a non-ionic X-ray contrast agent. Iodixanol was introduced in 1993, and is manufactured in large quantities. The production of this non-ionic X-ray contrast agent includes chemical manufacturing (primary production) and the manufacture of pharmaceutical preparations (secondary production); the primary production of iodixanol includes a multi-step chemical synthesis and is completed by a purification process.

Iodixanol for injection is directly injected into human blood vessels at very high dosages, which means that a very high quality for the iodixanol used as the raw material in secondary production is required. Hence the purity of the iodixanol should conveniently be even higher than that of the United States Pharmacopoeia standards. Notwithstanding, the efficiency and economy of primary production of commercial pharmaceutical products is equally important. Hence improvements in the chemical synthesis and the purification process of iodixanol is very important.

The chemical synthesis and the purification process of iodixanol can be both independent and associated with each other.

The literature cites in recent years many ways to prepare iodixanol. These include multi-step chemical synthesis as well as chromatographic and non-chromatographic purification methods. The cost of the final product available in the Pharmacy has largely been dependent on these processes, hence it is important to optimize these processes from the viewpoint of economic effectiveness and environmental protection.

A. Synthesis of Iodixanol

All of the major chemical synthetic processes known for the preparation of iodixanol start with 5-nitroisophthalic acid. The first reported method was described in EP 0108638 wherein the final intermediate 5-acetamido-N,N'-bis(2,3-dihydroxypropyl)-2,4,6-triiodo-isophthalamide (hereinafter referred to as compound A) is reacted with a reagent such as epichlorohydrin or 1,3-dichloro-2-hydroxyl propane to form iodixanol (hereinafter this reaction is referred to as dimerization). See Scheme 1.

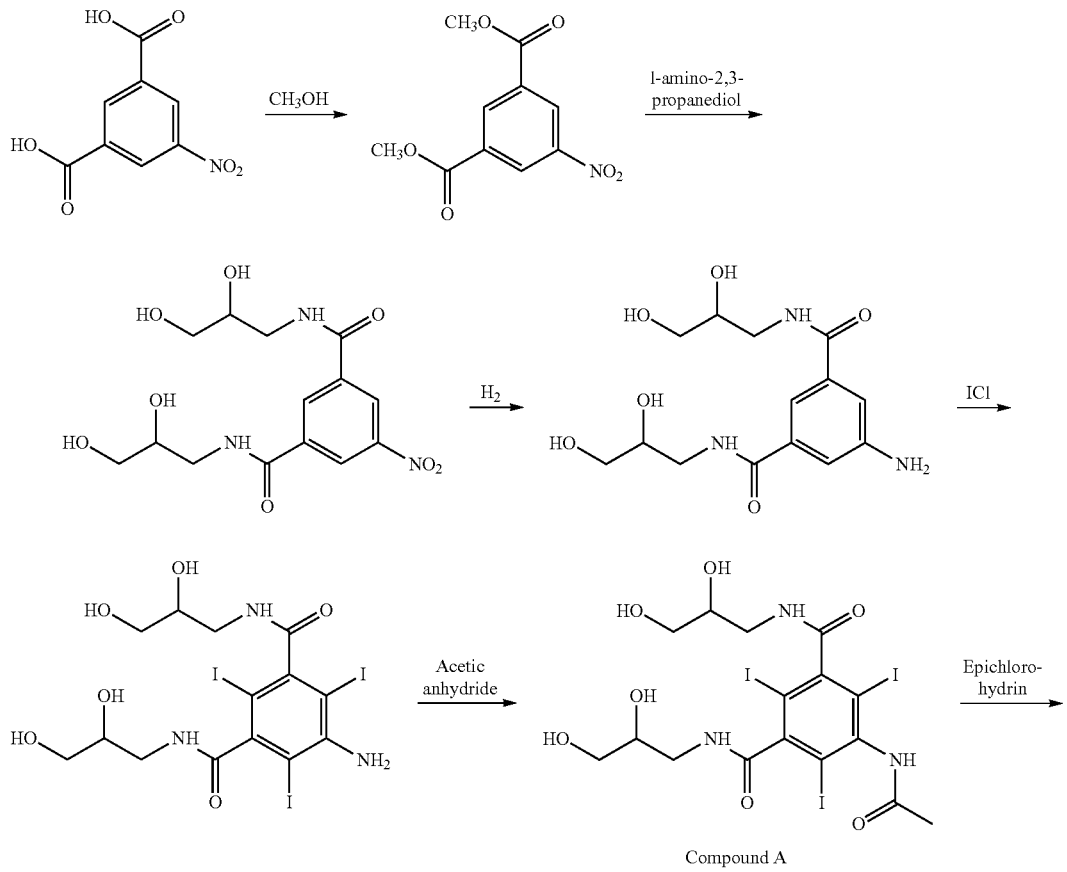

Scheme I

Compound A

-continued

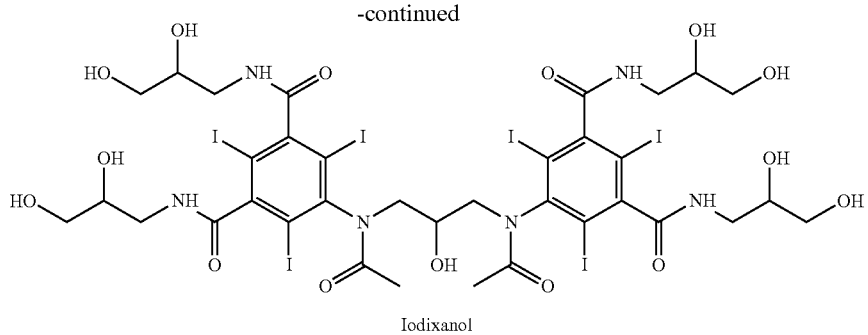

Iodixanol

The total yield of this process is relatively low and the purification process of the final product, iodixanol, is very expensive and time consuming. The purification processes described in EP 0108638 include the use of preparative liquid chromatography to carry out the purification. At the same time, the low purity of the product prepared by the method described also increases the difficulty of its purification. The use of preparative liquid chromatography makes it difficult to produce the product economically and efficiently in an industrial process. Production of large quantities is difficult.

Attempts have been made to find efficient and economical methods to prepare iodixanol. Priebe published an article (Acta Radioi. 36 (1995), Suppl 399, 21-31) attempting to increase the yield of the chemical synthesis. This article describes an alternative route to avoid difficulties in the dimerization shown in Scheme 1. However, this route involves eight reaction steps from 5-nitroisophthalic acid, one step includes a chlorination with thionyl chloride, which is a strongly corrosive. Also, the iodine atoms are introduced early in the synthetic route, which is disadvantageous as iodine is the most expensive regent in the process thus giving restricted opportunities to reduce the costs. The yield and final purification method of this route have not yet been reported.

The third synthetic route to prepare iodixanol prepares 5-amino-2,4,6-triiodo-isophthalic acid (WO 96/37458), which is then converted to its acid dichloride (WO 96/37459) then to compound A (U.S. Pat. No. 5,705,692) and finally dimerization carried out according to the process of Scheme 1. The difference between these two processes is that they use different routes to synthesis compound A. Hence this method has the same defects as the first synthesis process along with the undesirable acid chlorination step.

A fourth method to prepare iodixanol has been reported in KR 0050006367A and KR 050024944A. Compound A is firstly reacted with hydroxyl-protection reagent, then dimerization, and finally a de-protection step is carried out to prepare the iodixanol. This has two more reaction steps, but no increase of yield was reported although a reduction of O-alkylation was observed.

B. Purification Process of Iodixanol a). Chromatographic Purification Methods

EP 108638 describes the use of preparative liquid chromatography to carry out the purification. The use of RP-HPLC applied to a solution containing non-ionic compounds to decolorize, separate and purify contrast agents which are water-soluble and non-ionic are described in Mallinckrodt Inc.'s EP 0470247B1. Bracco S.p.A's EP 0902686B1 describes a refined purification method for contrast agents, including the joint application of chromatography and nanofiltration technology. Chromatography and nanofiltration is used on the crude solution to carry out the separations and then ion-exchange resin to carry out the decolourization.

Iodixanol can be purified to medicinal acceptable purity by any of the above-mentioned methods, which use preparative chromatography. The largest deficiency of these methods is that the cost of process may be increased and that the requirements for large scale manufactured cannot be met.

b). Non-Chromatographic Purification Methods

Several attempts to find alternative methods of purification to avoid liquid chromatographic methods described in EP 0108636.

WO 99/18054 describes a process for the crystallization of iodixanol where the crystallization is carried out using a high energy process, specifically under elevated pressure and at a temperature above the boiling point of the solution at atmospheric pressure.

WO 00/47549 describes a process to prepare iodixanol. Unreacted compound A may precipitate out from the reaction mixture, and recovered for reuse in the next batch thus increasing the total yield of the process. When most of the unreacted compound A is precipitated out from the reaction mixture, traditional crystallization, instead of high performance liquid chromatography, can be applied.

When iodixanol is crystallized from a mixture of methanol and 2-propanol (WO 9918054) with a small amount of residual water under reflux, the crystallization is slow and the purification effect is limited. To achieve the desired purity, the iodixanol crude product coming directly from the synthesis is crystallized twice. The process is time consuming and takes about 3 days for the first crystallization and about 2 days for the second.

WO 2006/016815 describes a method of purification by crystallization from 1-methoxy-2-propanol and water. WO 2007/064220 describes a method of purification by crystallization from a solution in ethanol and water. WO 2007/073202 describes a method of crystallization by using various solvents. In this method n-propanol or iso-propanol and water as purification solvents is described. However, the process is even more time consuming taking about three days and giving a yield of about 80-85%.

In CN 101293855A a large amount of polar solvents such as 2-methoxyethanol, ethanol and methanol are used to dissolve crude product. Then a small amount of a less polar solvent such as methyl acetate, ethyl acetate, acetonitrile are added to the solution until turbidity occurs. After slow cooling and crystallization iodixanol of increased purity is obtained.

This method needs to be repeated five times, and the total yield is only 30% or less. These methods do not have the high-performance and economy of preparation required and are difficult to reproduce on an industrial scale.

To sum up, a purity of iodixanol by HPLC of 75-90% is required before purification by crystallisation can be applied. However, the purity of the crude material from the synthetic sequence is generally 50-60%. Hence, it is necessary to improve the process to prepare iodixanol. The process of the chemical synthesis undoubtedly limits any improvement in the efficiency of the purification and the quality of the product.

CONTENTS OF THE INVENTION

This invention provides a method of preparation iodixanol, including efficient methods of synthesis and purification.

The invention includes the following features:

1. A method of preparation of iodixanol, characterized by comprising the following steps:
   a) dimerization of 5-acetamido-N,N'-bis (2,3-dihydroxypropyl)-2,4,6-triiodo-isophthalamide (compound A) to prepare iodixanol, obtaining a solution of dimerization;
   b) purification of the solution of dimerization by a macroporous adsorption resin chromatographic column, obtaining iodixanol crude product with a purity more than 97%; or
   desalination of the solution of dimerization by anionic and cationic ion exchange resins or macroporous adsorption resin chromatographic column, obtaining desalted iodixanol crude product;
   c) recrystallization of the iodixanol crude product with mixed solvents containing 2-methoxyethanol, obtaining iodixanol with a purity more than 99%.

The macroporous adsorption resin used in the method of the invention is nonpolar or weakly polar resin. The suitable resins may be a polystyrene based resin, pololyacrylic ester based resin, or a reticulated aliphatic polymer resin, preferably styrene-divinylbenzene copolymer based resin. The pore diameter of the resin is usually in the range of 80-300 Å. An example of the resin is a nonionic polymeric adsorption resin, including polyaromatic resins, such as, for example, Amberlite XAD-16, XAD-4, and the like. These resins function to remove impurities formed during the reaction process.

The anionic or cationic ion exchange resins used in the method of the invention is strong acid type cationic ion exchange resins, strong acid type or weak acid type anionic ion exchange resins. The weight ratio of the anionic or cationic ion exchange resins for the desalination and the iodixanol crude product is in the range of 20:1-0.2:1.

2. A method according to clause 1, wherein the iodixanol crude product obtained by desalination of the solution of dimerization contains 85-90% by weight of iodixanol, 3-7% by weight of iohexol, 2-5% by weight of compound A and other impurities.

3. A method according to clause 1, wherein the dimerization agent is epichlorohydrin, 1,3-dichloro-2-hydroxypropane or 1, 3-dibromo-2-hydroxypropane, and the dimerization reaction takes place in non-aqueous solvent, water, or mixture of water and one or more alcohols.

4. A method according to clause 3, wherein the dimerization agent is epichlorohydrin, and the solvent is water, 2-methoxyethanol or methanol, preferably water.

5. A method according to clause 3 or 4, wherein the ratio of the dimerization agent/compound A is 0.45-0.60 mole dimerization agent per mole compound A.

6. A method according to clause 1, wherein an excessive amount of alkali is used to dissolve compound A, followed by the neutralization of the excess alkali by a boron-containing acidic substance or salts thereof, adjusting the pH to 10-13, preferably 10-11.

7. A method according to clause 6, wherein the alkali used is alkali metal hydroxides, preferably potassium hydroxide or sodium hydroxide, and the ratio of compound A/alkali is 1.05-1.60 molar of alkali per mol of the compound A.

8. A method according to clause 6, wherein the boron-containing acidic substance or salts thereof used to neutralize the excess alkali to form a buffer solution comprises a boron oxyacid, a mixed acid comprising a boron oxyacid, and borate, wherein said boron oxyacid is boric acid, metaboric acid, pyroboric acid or tetraboric acid, said mixed acid comprising boron oxyacid comprises another acid selected from a group consisting of acetic acid, hydrochloric acid, phosphoric acid, sulphuric acid and a mixture thereof, said borate is selected from borax and metaborate such as sodium metaborate or potassium metaborate, preferably said boron-containing acidic substance or salts thereof is boric acid, a mixed acid comprising boric acid and hydrochloric acid and a mixed acid comprising boric acid and phosphoric acid.

9. A method according to clause 8, wherein the ratio of compound A/boron in the boron-containing acidic substance or salts thereof is 0.2-1.2 mole of boron per mole of compound A, preferably 0.2-0.8 of boron per mole of compound A.

10. A method according to claim 1, wherein the prepared iodixanol crude product is desalted by anionic and cationic ion exchange resins or a macroporous adsorption resin chromatographic column.

11. A method according to clause 10, wherein the purification of iodixanol crude product is achieved using a macroporous adsorption resin chromatographic column to separate inorganic and organic impurities.

12. A method according to clause 1, wherein the purified iodixanol by recrystallization has a global content of impurities content not higher than 0.2%.

13. A method according to clause 10 or 11, wherein the macroporous adsorption resin of the chromatographic column is a polystyrene based resin, pololyacrylic ester based resin, or a reticulated aliphatic polymer resin, preferably styrene-divinylbenzene copolymer based resin.

14. A method according to clause 10 or 11, wherein the weight ratio of the macroporous adsorption resin and iodixanol crude product is 20:1-2:1.

15. A method according to clause 10 or 11, wherein the weight ratio of the macroporous adsorption resin and iodixanol crude product is 2:1-0.5:1.

16. A method according to clause 11, wherein compound A and iohexol are isolated by using water or an aqueous solution with less than 5% alcohol to elute.

17. A method according to clause 11, wherein a larger quantity of water or an aqueous solution with less than 20% alcohol is used to elute, followed by nanofiltration and concentration of the filtrate, obtaining iodixanol crude product with a content of more than 97% iodixanol.

18. A method according to clause 11 wherein a aqueous solution with more than 30% alcohol is used to elute, followed by concentration to recover residues of iodixanol.

19. A method according to clause 16, 17 or 18, wherein the alcohol used to elute is C1 to C3 alkanol, preferably methanol.

20. A method according to clause 16, 17 or 18, wherein the elution is carried out under normal pressure or under a pressure, preferably 1.5 MPa.

21. A method according to clause 16, wherein the isolated compound A and iohexol are used to prepare iohexol, which is purified by the macroporous adsorption resin chromatographic column and the recrystallization with mixed solvents containing 2-methoxyethanol as defined in clause 1, obtaining iohexol which meeting the USP requirements for iohexol.

22. A method according to clause 1, wherein the iodixanol crude product used for the recrystallization is the solution of dimerization or the desalted aqueous solution thereof or a solid thereof obtained by spray-drying.

23. A method according to clause 1, wherein the recrystallization time is 1-4 days, preferably 1-3 days, more preferably about 1-2 days.

24. A method according to clause 1, wherein the temperature of recrystallization is above 60° C., preferably about 90-120° C., and more preferably 102-115° C.

25. A method according to clause 1, wherein the mixed solvent for the recrystallization contains 2-methoxyethanol, water and co-solvent, and the co-solvent is a C1 to C4 alkanol or a mixture thereof.

26. A method according to clause 25, wherein the co-solvent is ethanol, iso-propanol, n-butanol, sec-butanol, t-butyl alcohol or their mixtures, preferably n-butanol or iso-propanol.

27. A method according to clause 1, wherein the mixed solvent for the recrystallization include a mixed solvent of 2-methoxyethanol and iso-propyl alcohol, or 2-methoxyethanol and n-butanol.

28. A method according to clause 1, wherein the ratio of the mixed solvent for recrystallization/iodixanol crude product is about 1 to 30 grams of mixed solvent per gram of iodixanol crude product, preferably 2 to 10 grams.

29. A method according to clause 25, wherein the composition of the mixed solvent for the crystallization is 0.2-50 grams of co-solvent per gram of 2-methoxyethanol, preferably 0.8-8 grams of co-solvent.

30. A method according to clause 25, wherein the ratio of the mixed solvents for recrystallization/water is 1-100 grams of mixed solvent per gram of water, preferably 15-50 grams.

31. A method according to clause 1, wherein the recovered product which contains more than 20% iodixanol is purified by the macroporous adsorption resin chromatographic column, obtaining iodixanol crude product with a content of more than 97% iodixanol, wherein the recovered product with a iodixanol content of more than 20% is the residue in the macroporous adsorption resin chromatographic column, or is the refined mother liquor obtained after the recrystallization.

MODE OF CARRYING OUT THE INVENTION

The aim of this invention is to improve the synthetic method, starting from 5-acetyl-amino-N,N'-bis(2,3-dihydroxypropyl)-2,4,6-triiodo-isophthalamide (compound A) to prepare iodixanol. The basis of the improvement involves effectively curbing the formation of O-alkylated impurities and increasing the conversion rate to iodixanol thus giving an improved method of preparing iodixanol. From this base a new and efficient method of purification of iodixanol is provided, which not only makes the final product, iodixanol, meet USP requirements the costs are significantly reduced and the product can be manufactured in large quantities.

The above purpose is achieved according to synthetic route of Scheme I, by the N-alkylation of compound A to obtain iodixanol crude product ("dimerization"), followed by further purification to meet the requirements of the pharmacopoeia monographs. Surprisingly in this process it has been found that by using an excessive amount of alkali solution to dissolved compound A and then neutralizing the alkali in excess with, for example, a boron-containing acidic substance or salts thereof to form a buffer solution to adjust the pH to 10-13, preferably 10-11, a reaction mixture can be obtained which contains 85-90% iodixanol. Purification by use of a macroporous adsorption resin chromatographic column gives a crude product which contains more than 97% iodixanol, or desalination by use of anionic and cationic ion exchange resins or a macroporous adsorption resin chromatographic column gives desalted iodixanol crude product. Finally, the use of a mixed solvent system containing 2-methoxyethanol to recrystallize the crude product gives iodixanol, which meets pharmacopoeia requirements. Thus productivity is increased and costs reduced, meeting the requirements of an industrially viable process as well as achieving a number of improvements listed above.

The crude product from the process described in the synthetic route of Scheme I of dimerization is obtained as follows. The dimerization, which is achieved in the same fashion as described in EP 0108638 and WO 98/23296 uses epichlorohydrin, 1,3-dichloro-2-hydroxy-propane or 1,3-dibromo-2-hydroxy-propane as the dimerization reagent. This reaction is usually carried out in non-aqueous solvents, such as 1-6 carbon alcohols, especially 2-methoxyethanol and/or methanol but can also be carried out in aqueous solvents, preferably water, or can be carried out in a mixed solvent of water and one or more alcohols such as 1-6 carbon alcohols.

Initially, an excess of alkali (e.g. 1.05-1.60 mol) is used to dissolve compound A. This is followed by the addition of, for example, a mixed acid comprising a boron oxyacid, preferably boric acid, in a suitable amount to control the pH value and then a small excess of the dimerization reagent is added. The reaction to give O-alkylated by-products is effectively inhibited by the buffer solution which is formed with the salt of the boron oxyacid, preferably boric acid. In this way 85%-90% of compound A is transformed into iodixanol and 3-10% compound A to iohexol. Unreacted compound A is typically only 3-5% whilst other impurities are below 3%. This addresses the problem present in WO 00/47594, i.e., only 40-60% of Compound A can be converted to iodixanol and the a large quantity of unreacted Compound A has to be separated using lengthy procedures. This invention not only reduces the degree of difficulty in the purification of the crude product but also dramatically improves the efficiency of the production.

Thereafter, the dimerization reaction mixture is treated with macroporous adsorption resin chromatographic column chromatography to successfully complete the separation of impurities such as inorganic salts, compound A, iohexol and O-alkylated compounds. Thus the content of iodixanol is increased to 96-98%, typically greater than 97% in the crude product. In the separation and purification process the resin column is firstly eluted with water to separate inorganic salts. Water or a 5% aqueous solution of methanol is used to elute and recover compound A and iohexol. A larger quantity of water or lesser quantity of a 20% aqueous solution of methanol is used to elute iodixanol. Nanofiltration followed by vacuum distillation to concentrate the solution gives crude product containing 96-98%, typically greater than 97% iodixanol. A further fraction of iodixanol can be recovered from the column by continuing the elution with 20% or more aqueous methanol followed by concentration and repeating the resin column treatment 1-2 times. This gives iodixanol which is 96-98% pure, typically greater than 97%. The total recovery rate of purified iodixanol from the resin column is 90-95%.

Preferably, the crude product selected for solvent refining, preferably crystallization has been treated for the removal of salts from the reaction by anionic and cationic ion exchange resins or purified by the macroporous adsorption resin chromatographic column.

The crude product after removal of the salts contains 85-90% of iodixanol, 3-10% of iohexol, 3-5% of compound A and 3% of other impurities. After the crude product is purified by the resin column it contains 96-98%, typically greater than 97% of iodixanol, 0.5-2% of iohexol, 0.5-2% of compound A and a small quantity of other impurities. Further purification of the crude product is performed by crystallization from a mixed solvent system comprising of 2-methoxyethanol, followed by conventional processes well known in this field.

In addition to 2-methoxyethanol, the solvent system used in the solvent purification also contains water and another co-solvent. The co-solvent can be C1 to C4 alkanols or mixture thereof, e.g., methanol, ethanol, iso-propanol, n-butanol, sec-butanol, t-butyl alcohol and/or their mixtures, optimally n-butanol and iso-propyl alcohol.

If the water content of the aqueous solution containing iodixanol crude product, has to be adjust to the required levels, excess water can be remove by adding co-solvent such as n-butanol and carrying out an azeotropic distillation or distillation to complete dryness. Optimally, when the water content is higher than the desired level the azeotropic distillation to reduce the water content is carried out using distillation columns. Thereafter, 2-methoxyethanol and co-solvent, which is calculated after adjusting the water content, can be added to obtain the desired level. The content of water and mixed solvent depends on the initial quantity of iodixanol present. The range of mixed solvents/water should be 1-100 grams mixed solvent per of gram water, preferably 15-50 grams. The composition of the mixture for the crystallization is 0.2-50 grams co-solvent per gram of 2-methoxyethanol, preferably 0.8-8 grams of co-solvent. The range of mixed solvents/crude product should be about 1-30 grams of mixed solvents per grams of crude product, preferably 2-10 grams of mixed solvents.

Preferably 2-methoxyethanol and iso-propyl alcohol are used as a mixed solvent for the crystallize. Another preferable mixture is 2-methoxyethanol and n-butanol to carry out the crystallize.

The lower limit of the content of 2-methoxyethanol is important to ensure the iodixanol crude product is easily dissolved prior to crystallization. The upper limit of for the content of 2-methoxyethanol is important so that the formation of crystalline of iodixanol is ensured rather than amorphous solid. The crystallization temperature is above 60° C., preferably 90-120 ° C., more preferably 102-115 ° C.

In the initial crystallization process, the solvent is added in one portion and crystallisation allowed to proceed slowly to avoid the encapsulation of the highly viscous oil, thereby enhancing the purity of the product. The crystals are then filtered and washed with an alcohol, preferably methanol. It takes 1-4 days for the entire purification process 1-3 days being typical, more preferably 1-2 days, but usually about 2 days is sufficient.

The crude product is purified by crystallization from a mixed solvent system, which contains 2-methoxyethanol, giving high purity iodixanol whose purity is higher than Pharmacopoeia standards (>99%), and with a recovery rate of iodixanol about 90-95%.

The refined mother liquors obtained from the crystallization, which contain 40-60% of iodixanol, 20-40% of iohexol, 10-20% of compound A and a small amount of other impurities, can be used to obtain iodixanol crude product with a purity of 96-98%, typically greater than 97% after purifying 1-2 times using the macroporous adsorption resin chromatographic column.

The purity of iodixanol obtained from the solvent comprising 2-methoxyethanol is higher than expected. As explained above, this purification process involves filtration of the precipitated iodixanol from the solution, whereupon the crystals so obtained are washed with an alcoholic solvent such as methanol. The efficiency of the filtration and washing process depends on size and shape of crystals of iodixanol. It is surprising that the crystals obtained from the method described in this invention are easier and faster to filter and wash.

A still further embodiment of the invention provides iodixanol as obtained by the process of the invention where the iodixanol is of a purity fulfilling the specification of the US Pharmacopoeia.

The invention will now be described further with reference to the following non-limiting examples.

EXAMPLES

Yields in % is a weight percentage other than when another nomenclature is used.

In the following examples, Compound A was obtained according to the synthetic route known in the art and all the other reagents were obtained from commercial suppliers.

Example 1

Compound A (1120.5 kg, 1.50 kmol) was dissolved in a solution of KOH (140.0 kg, 2.25 kmol) in water (1232.6 kg), the temperature was controlled to below 20° C., boric acid (64.9 kg, 1.05 kmol) was equally added in a batch manner, and hydrochloric acid (30.4 kg, 0.30 kmol) was added dropwise, followed by epichlorohydrin (83.3 kg, 0.90 kmol), which was added dropwise. The pH during the reaction is 10-11. The reaction was monitored and a sample was analyzed by HPLC. The reaction was quenched by adding water (1232.6 kg) and adjusting the pH to within the range 5-6 with 18% of hydrochloric acid when the content of Compound A was below 5%.

The reaction mixture was then decolorized with active charcoal and filtered. The filtrate contained 86.3% of iodixanol, 7.5% of iohexol, 2.9% of compound A and 2.7% of O-alkylated by-products and other impurities by HPLC analysis.

Example 2

Compound A (1120.5 kg, 1.50 kmol) was dissolved in a solution of NaOH (78.0 kg, 1.95 kmol) in water (1232.6 kg), the temperature was controlled to below 20° C., boric acid (51.0 kg, 0.83 kmol) was equally added in a batch manner, and hydrochloric acid (23.3 kg, 0.23 kmol) was added dropwise, followed by epichlorohydrin (83.3 kg, 0.90 kmol), which was added dropwise. The pH during the reaction is 10-11. The reaction was monitored and a sample was analyzed by HPLC. The reaction was quenched by adding water (1232.6 kg) and adjusting the pH to within the range 5-6 with 18% of hydrochloric acid when compound A content was below 5%.

The inorganic ions were removed by passing through a column containing anionic and cationic ion exchange resins and then decolorized with active charcoal; the filtrate was concentrated by evaporation to dryness giving iodixanol crude product (1163.0 kg).

The contents by HPLC were 85.0% of iodixanol, 7.1% of iohexol, 3.0% of compound A, 2.9% of O-alkylated by-products and a small quantity of other impurities.

Example 3

Compound A (11.2 kg, 15.0 mol) was dissolved in a solution of NaOH (0.96 kg, 24.0 mol) in 2-methoxyethanol, the temperature was controlled to below 20° C., boric acid (0.65 kg, 10.5 mol) was equally added in a batch manner, and hydrochloric acid (0.55 kg, 5.4 mol) was added dropwise, followed by epichlorohydrin (0.75 kg, 8.1 mol), added dropwise. The pH during the reaction is 10-11. The reaction was monitored and a sample analyzed by HPLC. The reaction was quenched by adding water (12.3 kg) and adjusting the pH to within the range 5-6 with 18% hydrochloric acid when the content of Compound A was below 5%.

The reaction mixture was then decolorized with active carbon. The filtrate contained 84.2% of iodixanol, 5.1% of iohexol, 4.8% of compound A and 2.5% of O-alkylated by-products and other impurities by HPLC analysis.

Example 4

Compound A (11.2 kg, 15.0 mol) was dissolved in a solution of KOH (1.34 kg, 22.0 mol) in water (12.3 kg), the temperature was controlled to below 20° C., boric acid (0.65 kg, 10.5 mol) was equally added in a batch manner, followed by epichlorohydrin (0.83 kg, 9.0 mol), which was added dropwise. The pH during the reaction is 10-11. The reaction was monitored and a sample was analyzed by HPLC. The reaction was quenched by adding water (12.3 kg) and adjusting the pH to within the range 5-6 with 18% of hydrochloric acid when the content of Compound A was below 5%.

The reaction mixture was then decolorized with active charcoal and filtered. The filtrate contained 86.2% of iodixanol, 5.1% of iohexol, 3.2% of compound A and 2.2% of O-alkylated by-products and other impurities by HPLC analysis.

Example 5

Compound A (11.2 kg, 15.0 mol) was dissolved in a solution of NaOH (0.96 kg, 24.0 mol) in water (12.3 kg), the temperature was controlled to below 20° C., boric acid (0.65 kg, 10.5 mol) was equally added in a batch manner, and 85% phosphoric acid (0.21 kg, 1.8 mol) was added dropwise. After 5 hours further stirring, epichlorohydrin (0.75 kg, 8.1 mol) was added dropwise. The pH during the reaction is 10-11. The reaction was monitored and a sample was analyzed by HPLC. The reaction was quenched by adding water (12.3 kg) and adjusting the pH to within the range 5-6 with 18% of hydrochloric acid when the content of Compound A was below 5%.

The reaction mixture was then decolorized with active charcoal and filtered. The filtrate contained 83.2% of iodixanol, 6.1% of iohexol, 4.8% of compound A and 2.7% of O-alkylated by-products and other impurities by HPLC analysis.

Comparative Example 1

According to the Method of WO 00/47549

Compound A (11.2 g, 15.0 mmol) was dissolved in a solution of NaOH (0.82 g, 20.55 mol) in 2-methoxyethanol (12.3 kg), the temperature was controlled to below 20° C., hydrochloric acid (1.02 g, 10.1 mmol) was added dropwise and followed by epichlorohydrin (0.75 g, 8.1 mmol), which was added dropwise. After 1 day's reaction, the sample was analyzed by HPLC, which contained 55.77% of iodixanol, 1.28% of iohexol, 33.5% of compound A and 2.06% of O-alkylated by-products and other impurities by HPLC analysis. After 7 days' further reaction, the reaction was quenched by adding water (12.3 kg) and adjusting the pH to within the range 5-6 with 18% of hydrochloric acid.

The reaction mixture was then decolorized with active charcoal and filtered. The filtrate contained 69.1% of iodixanol, 2.60% of iohexol, 18.31% of compound A and 9.41% of O-alkylated by-products and other impurities by HPLC analysis.

It is clear from the above examples and comparative example that the conversion of Compound A to iodixanol has been greatly increased in the method of the invention.

Example 6

300 kg iodixanol crude product as described in Example 2 was added to a solution containing 900 kg of 2-methoxyethanol, 1500 kg n-butanol and 72 kg water at 70° C., the mixture was then brought to reflux, after the crude product was dissolved completely and the solution was transparent, 0.24 g of crystalline iodixanol seeds were added to the clear solution and the mixture was stirred under reflux during the whole crystallization process. 10 hours after the initial equilibration, an additional 300 kg of solvent containing 2-methoxyethanol and n-butanol, mixed in the same proportion as above, were continuously added to the crystallizing mixture during 28 hours. After an additional 6 hours the crystallization was complete. The crystal were filtered, washed with methanol and dried. 226.4 kg of crystalline iodixanol with a purity of 98.0% were obtained representing 87% yield from the crude product. The results of HPLC (water/acetonitrile, RP-18 column) analysis are presented in Table 1.

TABLE 1

Results of HPLC analysis (peak area percentage, %)

| Peak | Iodixanol | Compound A | Iohexol | Other impurities |
| --- | --- | --- | --- | --- |
| before recrystallization | 86.3 | 2.90 | 7.5 | 2.7 |
| after recrystallization | 98.0 | 0.45 | 1.12 | 0.43 |

Example 7

300 kg iodixanol crude product as described in example 2 was added to a solution containing 900 kg of 2-methoxyethanol, 1500 kg n-butanol and 72 kg water at 90° C., the mixture was then brought to reflux. After the crude product dissolved completely and the solution was transparent, 0.24 g of crystalline iodixanol seeds were added to the clear solution and the mixture stirred under reflux during the whole crystallization. 10 hours after of the initial equilibration an additional 300 kg of solvent containing 2-methoxyethanol and n-butanol, mixed in the same proportion were continuously added to the crystallizing mixture during 28 hours. After an additional 6 hours crystallization was complete. The crystals were filtered, washed with methanol and dried. 233.0 kg of crystalline iodixanol with a purity of 98.5% was obtained representing a 90% yield from the crude product. The results of HPLC (water/acetonitrile, RP-18 column) analysis are represented in Table 2.

A second crystallization of 200 kg of this iodixanol by the same crystallization process using the same mixed solvent system and the same unit operation gave 187.2 kg of crystalline iodixanol with a purity of 99.38% representing 95% yield. The results of HPLC (water/acetonitrile, RP-18 column) analysis are presented in Table 2.

TABLE 2

Results of HPLC analysis (peak area percentage, %)

| Peak | Iodixanol | Compound A | Iohexol | Other impurities |
| --- | --- | --- | --- | --- |
| before the first recrystallization | 85.0 | 2.9 | 7.1 | 3.0 |
| after the first recrystallization | 98.5 | 0.43 | 0.76 | 0.31 |
| after the second recrystallization | 99.67 | 0.06 | 0.001 | 0.27 |

Example 8

2400 kg crude iodixanol solution obtained by the method described in Example 1 and containing 500 kg of iodixanol (about 86.3% of iodixanol, 7.5% of iohexol, 2.9% of compound A and 2.7% O-alkylation and other impurities), was fed to three columns (φ600×5000×3) containing macroporous adsorption resin (Amberlite XAD-16 resin) and eluted with deionized water; the effluent was passed through a flow-cell for continuous measurement of conductivity and monitored by TLC. Inorganic salt and small organic molecules were eluted first from the column and discharged to effluent treatment. When fluorescence was obtained by spotting the solution on TLC plates HPLC analysis was carried out. The eluant containing iodixanol was collected content up until the iodixanol content rose to above 50%. The eluant was concentrated by nanofiltration and 54 kg of recovered desalinated material was obtained containing mainly compound A and iohexol. The column was then washed continuously with a large amount of deionized water and the eluate concentrated by nanofiltration then by vacuum distillation giving 375 kg of iodixanol (Part 1) with a purity of 97.68% representing 75% yield from the crude product. The gradient elution was continued with a 30% aqueous solution of methanol and the eluted solution concentrated and then vacuum distilled to give 70.8 kg of a second fraction of iodixanol. Repeating the column chromatography purification steps, 42.8 kg of iodixanol (Part 2) with a purity of 97.82% purity were obtained representing 8.56% yield from the 70.8 kg of recovered iodixanol crude product.

Combining Parts 1 and 2 gave 417.8 kg of pure iodixanol representing a yield of 83.6% from the crude product and 94.6% recovery of iodixanol This product was purified once more as described in Example 5 gave 384 kg of final iodixanol product and provided a drug substance fulfilling specification as expressed in the US Pharmacopoeia.

The yield of above steps and the results of HPLC were presented in Table 3.

TABLE 3

The results of HPLC analysis (peak area percentage, %)

| Products | Weight kg | Yield | Compound A (%) | Iohexol (%) | Iodixanol (%) | O-alkylated compounds (%) | Other impurities (%) |
|---|---|---|---|---|---|---|---|
| iodixanol crude product | 500 | | 2.90 | 7.5 | 86.3 | 2.5 | 0.80 |
| product (1) purified by column | 375 | 94.6% | 0.56 | 1.51 | 97.68 | 0.04 | 0.21 |
| product (2) purified by column | 42.8 | | 0.33 | 1.13 | 97.82 | 0.06 | 0.66 |
| end-product of the solvent refining | 384 | 94.3% | 0.05 | 0.002 | 99.80 | 0.03 | 0.12 |
| recovered product washed with an alcohol | 70.8 | | 0.23 | 0.76 | 79.60 | 16.7 | 2.1 |
| residue from the column purification | 23 | | 0.10 | 0.27 | 55.3 | 46.5 | 4.7 |
| recovered product from the desalination | 54 | | 22.6 | 56.8 | 10.79 | 0.28 | 3.22 |

The invention claimed is:

1. A method of preparation of iodixanol, characterized by comprising the following steps:
   a) dimerization of 5-acetamido-N,N'-bis (2,3-dihydroxypropyl)-2,4,6-triiodo-isophthalamide (compound A) to prepare iodixanol, obtaining a solution of dimerization; wherein said dimerization step comprises dissolving Compound A in an excessive amount of alkali, neutralizing the excess alkali by a boron-containing acidic substance of salts thereof, and adjusting the pH to 10-13;
   b) purification of the solution of dimerization by a macroporous adsorption resin chromatographic column, obtaining iodixanol crude product with a purity more than 97%; or
   desalination of the solution of dimerization by anionic and cationic ion exchange resins or macroporous adsorption resin chromatographic column, obtaining desalted iodixanol crude product;
   c) recrystallization of the iodixanol crude product with mixed solvents containing 2-methoxyethanol, obtaining iodixanol with a purity more than 99%.

2. A method according to claim 1, wherein the iodixanol crude product obtained by desalination of the solution of dimerization contains 85-90% by weight of iodixanol, 3-7% by weight of iohexol, 2-5% by weight of compound A and other impurities.

3. A method according to claim 1, wherein the dimerization agent is epichlorohydrin, 1,3-dichloro-2-hydroxypropane or 1,3-dibromo-2-hydroxypropane, and the dimerization reaction takes place in non-aqueous solvent, water, or mixture of water and one or more alcohols.

4. A method according to claim 3, wherein the dimerization agent is epichlorohydrin, and the solvent is water, 2-methoxyethanol or methanol.

5. A method according to claim 3 or 4, wherein the ratio of the dimerization agent/compound A is 0.45-0.60 mole dimerization agent per mole compound A.

6. A method according to claim 1, wherein the alkali used is alkali metal hydroxides, and the ratio of compound A/alkali is 1.05-1.60 molar of alkali per mol of the compound A.

7. A method according to claim 6, wherein the boron-containing acidic substance or salts thereof used to neutralize the excess alkali to form a buffer solution comprises a boron oxyacid, a mixed acid comprising a boron oxyacid, and borate, wherein said boron oxyacid is boric acid, metaboric acid, pyroboric acid or tetraboric acid, said mixed acid comprising boron oxyacid comprises another acid selected from a group consisting of acetic acid, hydrochloric acid, phosphoric acid, sulphuric acid and a mixture thereof, said borate is selected from borax and metaborate, a mixed acid comprising boric acid and hydrochloric acid and a mixed acid comprising boric acid and phosphoric acid.

8. A method according to claim 7, wherein the ratio of compound A/boron in the boron-containing acidic substance or salts thereof is 0.2-1.2 mole of boron per mole of compound A.

9. A method according to claim 1, wherein the prepared iodixanol crude product is desalted by anionic and cationic ion exchange resins or a macroporous adsorption resin chromatographic column.

10. A method according to claim 9, wherein the purification of iodixanol crude product is achieved using a macroporous adsorption resin chromatographic column to separate inorganic and organic impurities.

11. A method according to claim 1, wherein the purified iodixanol by recrystallization has a global content of impurities content not higher than 0.2%.

12. A method according to claim 9 or 10, wherein the macroporous adsorption resin of the chromatographic column is a polystyrene based resin, to pololyacrylic ester based resin, or a reticulated aliphatic polymer resin.

13. A method according to claim 9 or 10, wherein the weight ratio of the macroporous adsorption resin and iodixanol crude product is 20:1-2:1.

14. A method according to claim 9 or 10, wherein the weight ratio of the macroporous adsorption resin and iodixanol crude product is 2:1-0.5:1.

15. A method according to claim 10, wherein compound A and iohexol are isolated by using water or an aqueous solution with less than 5% alcohol to elute.

16. A method according to claim 10, wherein a larger quantity of water or an aqueous solution with less than 20% alcohol is used to elute, followed by nanofiltration and concentration of the filtrate, obtaining iodixanol crude product with a content of more than 97% iodixanol.

17. A method according to claim 10 wherein a aqueous solution with more than 30% alcohol is used to elute, followed by concentration to recover residues of iodixanol.

18. A method according to claim 15, 16 or 17, wherein the alcohol used to elute is C1 to C3 alkanol.

19. A method according to claim 15, 16 or 17, wherein the elution is carried out under normal pressure.

20. A method according to claim 15, wherein the isolated compound A and iohexol are used to prepare iohexol, which is purified by the macroporous adsorption resin chromatographic column and the recrystallization with mixed solvents containing 2-methoxyethanol as defined in claim 1, obtaining iohexol which meeting the USP requirements for iohexol.

21. A method according to claim 1, wherein the iodixanol crude product used for the recrystallization is the solution of dimerization or the desalted aqueous solution thereof or a solid thereof obtained by spray-drying.

22. A method according to claim 1, wherein the recrystallization time is 1-4 days.

23. A method according to claim 1, wherein the temperature of recrystallization is above 60° C.

24. A method according to claim 1, wherein the mixed solvent for the recrystallization contains 2-methoxyethanol, water and co-solvent, and the co-solvent is a C1 to C4 alkanol or a mixture thereof.

25. A method according to claim 24, wherein the co-solvent is ethanol, iso-propanol, n-butanol, sec-butanol, t-butyl alcohol or their mixtures.

26. A method according to claim 1, wherein the mixed solvent for the recrystallization include a mixed solvent of 2-methoxyethanol and iso-propyl alcohol, or 2-methoxyethanol and n-butanol.

27. A method according to claim 1, wherein the ratio of the mixed solvent for recrystallization/iodixanol crude product is about 1 to 30 grams of mixed solvent per gram of iodixanol crude product.

28. A method according to claim 24, wherein the composition of the mixed solvent for the crystallization is 0.2-50 grams of co-solvent per gram of 2-methoxyethanol.

29. A method according to claim 24, wherein the ratio of the mixed solvents for recrystallization/water is 1-100 grams of mixed solvent per gram of water.

30. A method according to claim 1, wherein the recovered product which contains more than 20% iodixanol is purified by the macroporous adsorption resin chromatographic column, obtaining iodixanol crude product with a content of more than 97% iodixanol, wherein the recovered product with a iodixanol content of more than 20% is the residue in the macroporous adsorption resin chromatographic column, or is the refined mother liquor obtained after the recrystallization.

31. A method according to claim 3, wherein the dimerization agent is epichlorohydrin, and the solvent is water.

32. A method according to claim 1, wherein the alkali used is potassium hydroxide.

33. A method according to claim 1, wherein the alkali used is sodium hydroxide.

34. The method of claim 7, wherein said borate comprises sodium metaborate.

35. The method of claim 7, wherein said borate comprises potassium metaborate.

36. The method of claim 7, wherein said boron-containing acidic substance or salts thereof is boric acid.

37. The method to claim 7, wherein the ratio of compound A/boron in the boron-containing acidic substance or salts thereof is 0.2-0.8 of boron per mole of compound A.

38. A method according to claim 9, wherein the macroporous adsorption resin of the chromatographic column is a styrene-divinylbenzene copolymer based resin.

39. A method according to claim 10, wherein the macroporous adsorption resin of the chromatographic column is a styrene-divinylbenzene copolymer based resin.

40. A method according to claim 15, wherein the alcohol used to elute is methanol.

41. A method according to claim 16, wherein the alcohol used to elute is methanol.

42. A method according to claim 17, wherein the alcohol used to elute is methanol.

43. A method according to claim 15, wherein the elution is carried out under pressure of 1.5 MPa.

44. A method according to claim 16, wherein the elution is carried out under pressure of 1.5 MPa.

45. A method according to claim 17, wherein the elution is carried out under pressure of 1.5 MPa.

46. A method according to claim 1, wherein the recrystallization time is 1-3 days.

47. A method according to claim 1, wherein the recrystallization time is 1-2 days.

48. A method according to claim 1, wherein the temperature of recrystallization is about 90-120° C.

49. A method according to claim 1, wherein the temperature of recrystallization is about 102-115° C.

50. A method according to claim 24, wherein the co-solvent is n-butanol.

51. A method according to claim 24, wherein the co-solvent is iso-propanol.

52. A method according to claim 1, wherein the ratio of the mixed solvent for recrystallization/iodixanol crude product is about 2 to 10 grams of mixed solvent per gram of iodixanol crude product.

53. A method according to claim 24, wherein the composition of the mixed solvent for the crystallization is 0.8-8 grams of co-solvent per gram of 2-methoxyethanol.

54. A method according to claim 25, wherein the ratio of the mixed solvents for recrystallization/water is 15-50 grams of mixed solvent per gram of water.

* * * * *

UNITED STATES PATENT AND TRADEMARK OFFICE
CERTIFICATE OF CORRECTION

| | |
|---|---|
| PATENT NO. | : 8,766,002 B2 |
| APPLICATION NO. | : 13/510432 |
| DATED | : July 1, 2014 |
| INVENTOR(S) | : Zhiqi Hu and Huoying Zhang |

Page 1 of 1

It is certified that error appears in the above-identified patent and that said Letters Patent is hereby corrected as shown below:

In the Claims

Column 14, Claim 7, Line 35, delete "6" and insert --1--.

Signed and Sealed this
Sixteenth Day of September, 2014

Michelle K. Lee
*Deputy Director of the United States Patent and Trademark Office*